United States Patent [19]
Davis et al.

[11] Patent Number: 5,836,952
[45] Date of Patent: Nov. 17, 1998

[54] HAND-HELD STENT CRIMPER

[75] Inventors: Horace R. Davis, Pembroke Pines; Phillip G. Reed, Davie, both of Fla.

[73] Assignee: Cordis Corporation, Miami Lakes, Fla.

[21] Appl. No.: 700,816

[22] Filed: Aug. 21, 1996

[51] Int. Cl.⁶ .................................................. A61F 11/00
[52] U.S. Cl. ................ 606/108; 606/1; 606/198
[58] Field of Search ................ 606/1, 108, 191, 606/194, 198; 53/204, 209, 211, 213, 214, 203

[56] References Cited

U.S. PATENT DOCUMENTS

| | | | |
|---|---|---|---|
| 1,306,354 | 6/1919 | Robbins | 279/48 |
| 1,765,362 | 6/1930 | Berry | 279/48 |
| 2,455,019 | 11/1948 | McNeill | 401/93 |
| 2,468,946 | 5/1949 | Sherman | 279/48 |
| 2,978,250 | 4/1961 | Abadjieff | 279/48 |
| 3,353,395 | 11/1967 | Rauch | 72/402 |
| 4,215,871 | 8/1980 | Hirsch et al. | 279/48 |
| 4,341,002 | 7/1982 | Diba | 29/235 |
| 4,553,545 | 11/1985 | Maass et al. | 606/198 |
| 5,096,111 | 3/1992 | Ishikawa et al. | 29/235 |
| 5,201,901 | 4/1993 | Harada et al. | 606/198 |
| 5,259,109 | 11/1993 | Fefeu et al. | 29/235 |
| 5,437,083 | 8/1995 | Williams et al. | 29/235 |
| 5,476,505 | 12/1995 | Limon | 623/1 |
| 5,626,604 | 5/1997 | Cottone, Jr. | 606/198 |
| 5,630,830 | 5/1997 | Verbeek | 606/198 |

*Primary Examiner*—Michael Buiz
*Assistant Examiner*—Julian W. Woo
*Attorney, Agent, or Firm*—Lockwood, Alex, Fitzgibbon & Cummings

[57] ABSTRACT

A stent crimper is provided for loading a stent onto a catheter in order to provide a stenting assembly that is suitable for use in procedures in conjunction with percutaneous transluminal angioplasty and percutaneous transluminal coronary angioplasty catheters. The crimper has a stent holding member or sheath which supports the stent by its exterior surface so that a balloon of a catheter can be slid within the stent. An elongated wrapping member or belt winds around the sheath. By properly manipulating the belt, the belt applies generally cylindrical radially directed forces onto the sheath and thus onto the stent within the sheath, as well as the balloon beneath the stent, in order to crimp the stent onto the balloon. A procedure is also illustrated by which a stent is crimped onto the balloon by a hand-held crimper which can be discarded after stent delivery and crimping has been completed.

33 Claims, 4 Drawing Sheets

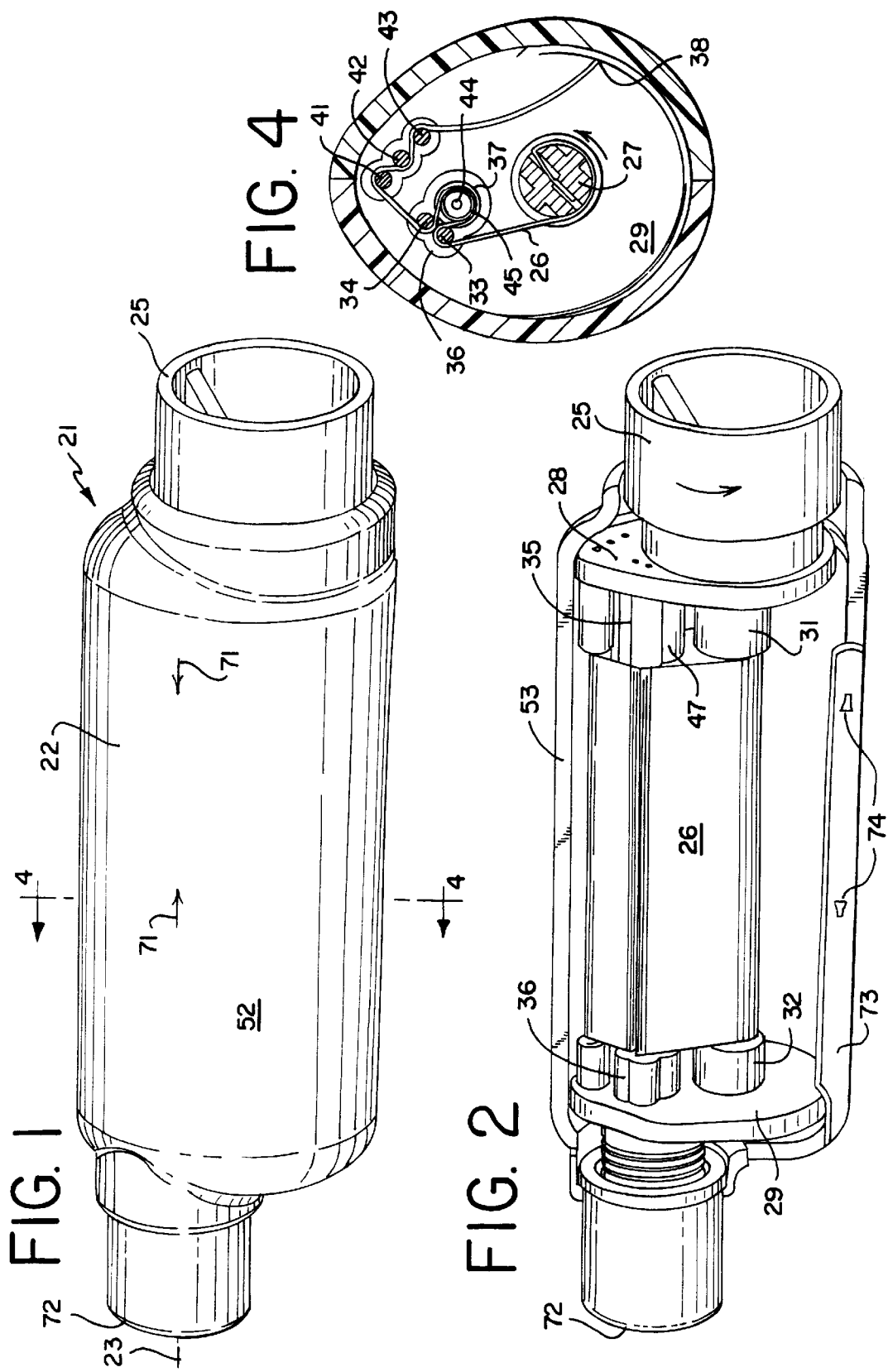

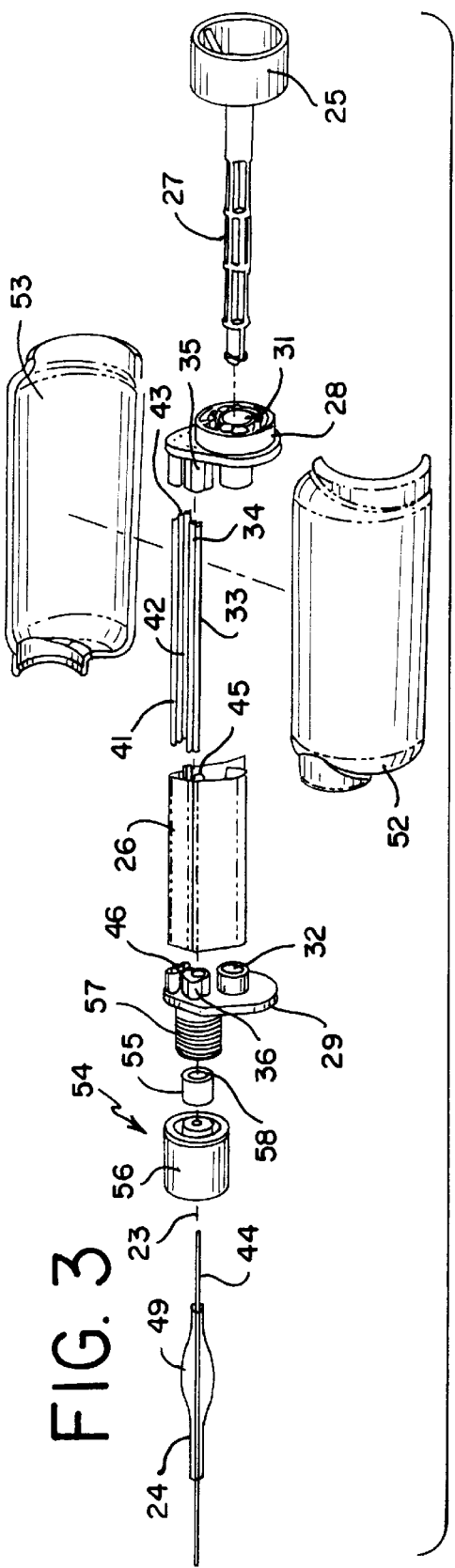
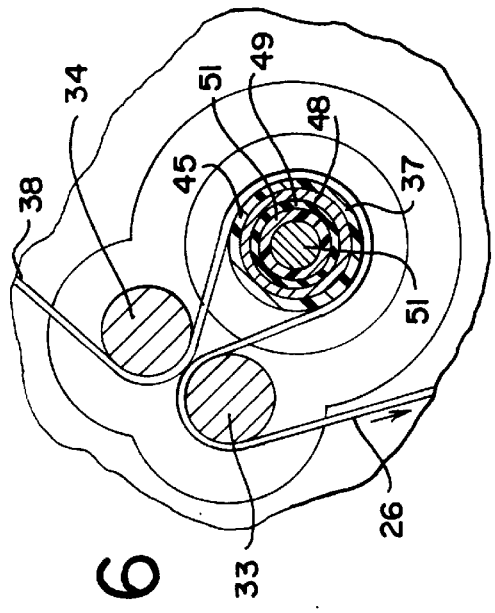
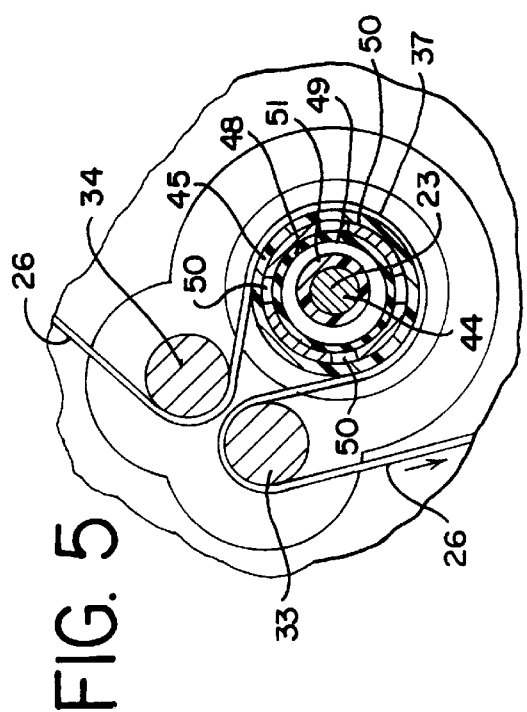

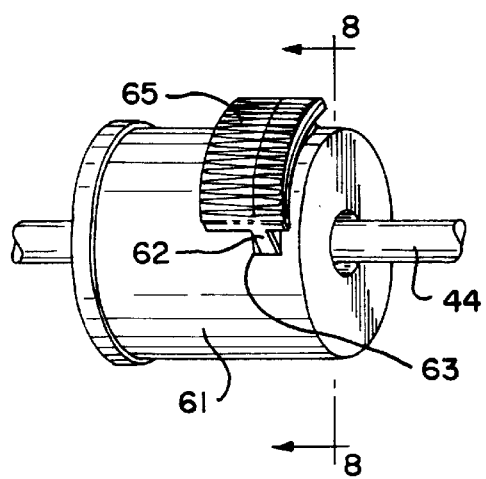
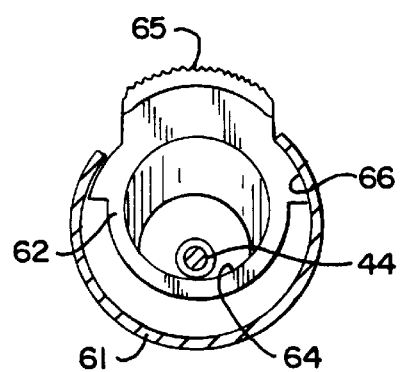
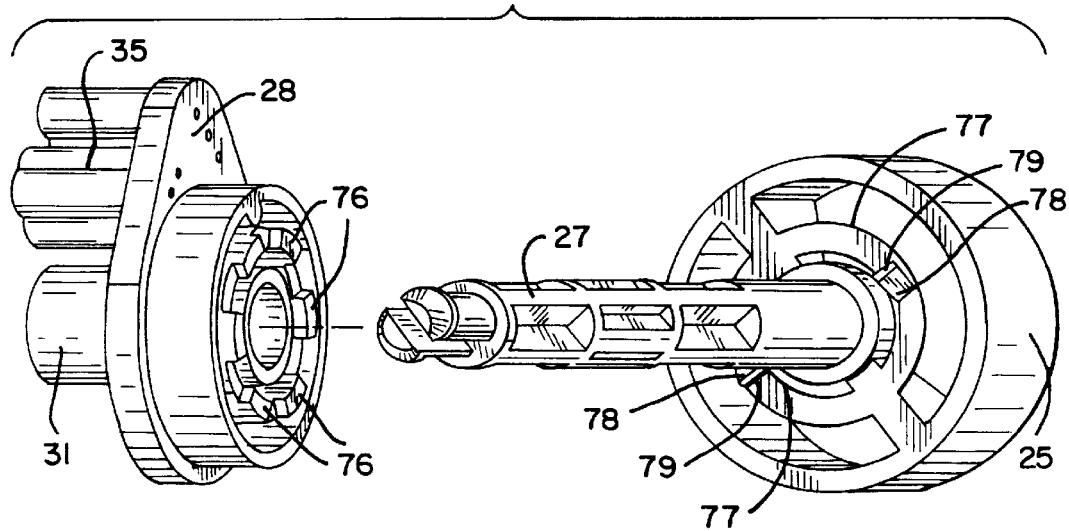

HAND-HELD STENT CRIMPER

FIELD OF THE INVENTION

The invention generally relates to crimpers and crimping procedures that provide consistent and uniform crimping of balloon-deployable devices onto catheter balloons by eliminating subjective factors during crimping. In particular, the invention is related to hand-held crimping devices which can be disposable and are used to load a stent or other balloon-deployable device onto the distal end of a balloon dilation catheter assembly. Additionally, the hand-held crimpers are very versatile in handling a wide range of diameter and length sizes of stents or the like such as those small enough to be suitable for coronary uses and those large enough for peripheral uses.

BACKGROUND OF THE INVENTION

A stent is an intravascular prosthesis that is generally introduced percutaneously, transported transluminally and positioned at a desired location within a patient. A stent typically is implanted during or closely after angioplasty in order to reduce the chance of restenosis and/or strengthen the vessel location undergoing angioplasty or other treatment. When it is of the balloon-launched type, the stent is transported to the treatment location by a balloon catheter and is implanted by expansion of the balloon when the balloon and stent are at the desired location. Expansion of the balloon portion of the catheter can simultaneously compress plaque at that location and expand the stent to its proper implantation size. The balloon portion of the catheter is then deflated and the catheter withdrawn, leaving the stent implanted. Alternative procedures are also possible and are known to those skilled in the art. Self-expanding stents can also be used in percutaneous transluminal angioplasty (PTA) and percutaneous transluminal coronary angioplasty (PTCA) procedures. Examples of stents useful in the PTA or PTCA procedures are described in U.S. Pat. No. 4,655,771 to Wallsten, U.S. Pat. No. 4,739,762 to Palmaz and U.S. Pat. No. 5,019,090 to Pinchuk. Other balloon-deployed devices are known. These include filters, catchers and the like.

In practicing stenting, stents of various diameters and lengths are used from procedure to procedure, the diameter and length of the stent being selected to correspond to the dimensions of the vessel location undergoing repair or treatment. Delivering the stent to the location undergoing repair or treatment requires the stent to have a low profile and to have been secured to the balloon catheter so that it does not slide off the catheter as it is being inserted and transported to the desired location within the patient. Similar needs exist for other balloon-deployed devices. Consequently, the stent or the like is typically crimped or otherwise secured about a catheter, such as over the balloon of a balloon catheter, before being inserted into the patient. Once at the treatment location, the stent or the like is expanded in a direction which generally reverses the crimping procedure, typically expanding even more than when at its pre-crimped configuration.

Crimped stents may be either pre-crimped about the catheter by the supplier or may be crimped on-site in sterile field by medical personnel. If stents pre-crimped about a catheter are used, generally a large stock of stent-bearing angioplasty catheters must be maintained in order to insure that one properly sized stent/catheter unit is available when it is needed. Maintaining such an inventory can be expensive. The inventory expense can be reduced by stocking separate catheters and stents, and having the surgical personnel crimp the desired stent about a selected catheter prior to a procedure. However, the proper crimping of a stent about a balloon catheter is a technique acquired only through practice and can be affected by a variety of subjective conditions. For example, stents can be crimped using sterile pliers. Excessive and/or cylindrically non-uniform force applied during crimping, such as when pliers are used, can damage the stent and/or the catheter. Crimping problems are also caused by the small size of the stents, which are typically about 3–4 millimeters (mm) in diameter before crimping and 1–10 centimeters (cm) in length or longer. Examples of the problems encountered are non-uniform crimping, the inability to judge when a reliable and uniform crimp has been achieved, and damage to the stent or catheter during crimping.

U.S. Pat. No. 5,437,083 describes a device for placing a stent about a balloon catheter. The device has a series of plates which have substantially flat and parallel surfaces that move in a rectilinear fashion with respect to each other. A stent carrying catheter can be disposed between these surfaces to affix the stent onto the outside of the catheter by relative motion between the plates. Force indicating transducers are used in conjunction with the plates to indicate the force being applied during affixation of the stent. This patent also describes an embodiment whereby a fluid filled bladder is used to crimp a stent about a balloon catheter. Although the device of this patent seems useful in a commercial setting, its use in a surgical theater is believed to impose some problems, particularly with regard to maintaining sterility.

With regard to the crimping of stents or the like onto catheters, there is a need for a simple device, preferably disposable, which would eliminate subjective factors during crimping, eliminate the handling of the stents themselves in the surgical theater, and solve the inventory problem. The present invention addresses these objectives by providing hand-held crimpers which are loaded with a stent or the like and which are structured to receive a catheter therewithin and in axial alignment with the stent or the like. An elongated wrapping member or belt exerts a generally cylindrical internally compressive force on the stent or the like in order to crimp it onto the desired location along the catheter. This crimping action is carried out by the simple unidirectional rotation of a knob.

It is accordingly a general object of the present invention to provide an improved device and procedure for crimping a device onto a catheter.

Another object of the present invention is to provide an improved crimping device and method which exerts a uniform radially compressive force onto the outer surface of any one of a variety of stents or the like having a wide range of diameters.

Another object of this invention is to provide an improved crimper and method which incorporates a rolling motion to allow the force to be distributed evenly to a generally cylindrical stent or similar device.

Another object of the present invention is to provide an improved stent crimper and method for packaging stents within a disposable device that also crimps the stent onto the balloon of an angioplasty catheter or the like.

Another object of the present invention is to provide an improved stent delivery device and procedure which accommodates angioplasty balloon catheters of all sizes.

Another object of this invention is to provide an improved crimper and procedure which requires minimal effort by the operator to crimp a stent or similar device onto a balloon catheter.

Another object of the present invention is to provide an improved stent crimping device and method in which a balloon catheter and a stent spin in the same direction, thus folding the balloon during the operation and allowing a uniform radial compressive force to be distributed evenly around the entire surface area of the stent.

Another object of the present invention is to provide a crimper and method by which the physician or medical professional neither touches nor is exposed to the stent or other device which is being crimped, such as when the device is radioactive or is coated with a medication, a protective coating or the like.

Another object of this invention is to provide an improved crimper and method which performs a crimping operation in one pass, during which the crimping sequence/user interface moves from a neutral action to a tensioned crimping action and back to a neutral action which indicates that the crimping has been completed, all while rotating a drive wheel in a single direction.

These and other objects, features and advantages of the present invention will be apparent from and clearly understood through a consideration of the following detailed description.

SUMMARY OF THE INVENTION

The invention is directed to devices for loading a stent or other balloon-deployable device onto a balloon catheter and crimping same in place about the catheter in a surgical theater while avoiding any contact of the stent or other device itself by the medical personnel. Reference herein will at times be made to a stent or to stents, and it should be understood that these terms also encompass other balloon-deployable devices which need to be crimped, for example filters such as vena cava filters and the like. The invention eliminates the subjective factors presently involved in stent crimping and eliminates the need for tools such as pliers which might damage the stent during the crimping operation.

The devices of the invention also preferably are disposable, eliminating the concerns associated with reusable devices including sterility and improper loading. Crimpers according to the invention also safely encase stents at the manufacturer level until the stents are conveniently inserted over and crimped onto the balloon catheter selected by medical personnel prior to delivery.

A hand-held crimping device according to the invention has a longitudinal feed axis which generally defines the operational orientation of the device and the longitudinal pathway along which the catheter is inserted to receive the stent. Generally positioned along this feed axis are a catheter guide, a stent holder or sheath, and a stent therewithin. An elongated wrapping member or belt having a width which extends for at least approximately the length of the stent to be crimped wraps substantially around the stent holder or sheath. A suitable moving and guiding mechanism tightens the wrapping member in order to cylindrically compress the sheath and the stent therewithin so as to effect the desired stent crimping in response to hand-applied digital forces imparted to the moving and driving mechanism by the person assembling the stent onto the catheter. Afterward, the catheter/stent assembly is easily removed from the crimping device leaving the stent only on the catheter so that the stent is ready for delivery into the patient by means of the catheter. Alternatively, the sheath could emerge from the crimping device together with the stent, particularly when the sheath plasticly deforms, thereby providing stress and strain relief, more uniform crimping and stent protection.

In a preferred embodiment, the moving and guiding mechanism of the present invention includes a drive shaft and knob unit to which one end of the wrapping member is secured, and the wrapping member moves over a pair of closely spaced pinch rollers generally adjacent and parallel to the sheath and offset from and generally parallel to the feed axis. In operation, the user rotates the knob which pulls the wrapping member through a guided pathway in order to exert the cylindrical compressive force on the sheath and thus on the stent therewithin. This pathway includes a compression site or compressive loop by which the wrapping member rides over one of the pinch rollers, then the sheath, and then the other of the pinch rollers so as to pass over the sheath and between the pinch rollers. Because the pinch rollers are stationary in the sense that each remains at its designated location within the device, tension in the wrapping member, which exerts a cylindrically compressive force on the sheath, collapses the sheath and the stent within it. In a typical arrangement, development of this tension is enhanced by a drag-imparting means which engages the wrapping member or belt at a location downstream of the pinch rollers, which is opposite to the drive shaft and knob unit along the wrapping member.

BRIEF DESCRIPTION OF THE DRAWINGS

FIG. 1 is a perspective view of a preferred hand-held stent crimper according to the invention;

FIG. 2 is a cut-away perspective view of the device illustrated in FIG. 1 and from which a housing component of the outer sleeve has been removed;

FIG. 3 is an exploded perspective view of the stent crimper illustrated in FIG. 1;

FIG. 4 is a cross-sectional view along the line 4—4 of FIG. 1;

FIG. 5 is a detail, cross-sectional view taken from FIG. 4 which illustrates this portion of the device prior to crimping;

FIG. 6 is a detail, cross-sectional view corresponding to FIG. 5, shown after crimping has taken place;

FIG. 7 is a perspective, cut-away view of an alternative embodiment of a gripping assembly at the catheter-insertion end of the device;

FIG. 8 is a cross-sectional view along the line 8—8 of FIG. 7;

FIG. 9 is an exploded perspective view illustrating an anti-reversing feature;

DETAILED DESCRIPTION OF THE INVENTION

Figure 10:
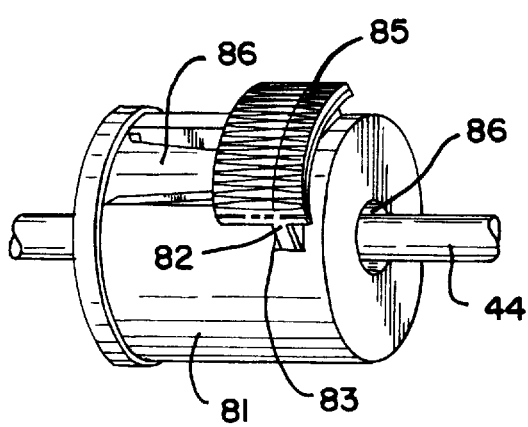
FIG. 10 is a perspective, cut-away view of a further embodiment of another catheter gripping assembly.

A crimper, generally designated at 21 in FIG. 1, includes an outer case 22 having a longitudinal feed axis 23 entering same as indicated. On an external level, crimping is accomplished by inserting a catheter 24 (FIG. 3) into the crimper 21 along the longitudinal feed axis 23 to a desired extent, as discussed more fully herein, followed by unidirectional rotation of a crimper knob 25. Crimping completion is indicated when the tension which develops during rotation of the crimper knob ceases.

With more particular reference to the internal operational details of the crimper illustrated in FIG. 1 through FIG. 6, an important operational component in this regard is the elongated wrapping member or belt 26. It is operated by means of a moving and guiding assembly which includes the crimper knob 25. The crimper knob is an extension of a drive shaft 27 which can conveniently be rotatably mounted between a base member 28 and a cap member 29, for example through openings 31, 32, respectively. It will be appreciated that the drive shaft 27 will rotate when the user rotates the crimper knob or drive wheel 25, the drive shaft rotating within the openings 31 and 32.

A further component of the moving and guiding assembly is the pair of closely spaced rollers 33 and 34, which operate in the nature of pinch rollers as described in greater detail herein. Pinch rollers 33 and 34 are mounted in a stationary manner by which each remains at its respective designated location within the device. Such stationary mounting allows for rotation of the pinch rollers 33 and 34, such as within the mounting ferrules 35 and 36. As evident from FIG. 4, the elongated wrapping member or belt 26 affixes to the drive shaft 27 and is threaded over the pinch rollers 33 and 34, forming a looped path portion between the closely spaced pinch rollers 33 and 34. Thus, when the belt is wrapped around the drive shaft 27, such as in the direction of the arrow shown in FIG. 4, the belt winds onto the drive shaft and is pulled over the pinch rollers 33 and 34 and through a looped path portion 37 which generally defines a compression site or compressive loop.

It is typically desired to impart extra drag to the belt when it is upstream of the pinch roller 34. This ensures that the looped path portion 37 will reduce in radial size and thereby effect crimping in accordance with the present invention. In the illustrated embodiment, this drag enhancement is achieved by a plurality of axles 41, 42 and 43 which are generally closely spaced to each other as illustrated. Belt 26 is fed between these stationary axles in an alternating fashion such as that shown in FIG. 4. This threading, in combination with the wrapping angles, imparts added friction against the belt 26. The resultant added drag nicely initiates and carries out the crimping as described herein. Furthermore, once the crimping has been completed, which means that the items being crimped no longer will be reduced radially by the action of the belt, the belt will continue to pass through the looped path portion 37 until the free end 38 of the belt clears some or all of the axles or rollers, at which time the crimper knob 25 moves freely, approximating a neutral drive condition.

With more particular reference to the components which lie along the longitudinal feed axis 23, a guide member or short guidewire 44 lies directly along the feed axis 23. This guide member 44 runs substantially the entire length of the crimper from the entry end to the base member 28. Substantially coaxial with the guide member 44 is a holding member or sheath 45. This sheath is externally supported at one or both of its ends so as to maintain its general coaxial relationship with the longitudinal feed axis 23 and the guide member 44. Sheath 45 may, for example, fit within opening 46 of the cap member 29 and/or a similar opening in the boss 47 of the base member 28. This holding or mounting of the sheath 45 allows for radially inwardly directed movement of the sheath in response to forces imparted by the belt 26 during rotation of the crimper knob 25.

A stent 48 (FIGS. 5 and 6) is shown located within and supported by the holding member or sheath 45. When the catheter 24 is inserted into the crimper 21, the orientation is such that the illustrated stent 48 overlies a balloon 49 (FIGS. 3, 5 and 6) of the catheter 24. Also shown in FIGS. 5 and 6 is a catheter tube 51. It will be noted that the catheter tube generally closely overlies the guide member 44, thereby facilitating proper axial placement of the catheter within the crimper 21 and coaxial with the feed axis.

In the illustrated embodiment, the outer case 22 of the crimper is composed of two components, a left housing 52 and right housing 53. It is important that the catheter 24 be inserted into the crimper for a proper distance so that the balloon 49 is in proper registry with the stent 48 or other device. Means for accomplishing this are discussed herein. Once the proper positioning is thus achieved, it is useful to provide a gripping arrangement in order to hold the catheter in place prior to and during the crimping operation that is performed by the crimper. The gripping mechanism illustrated in FIG. 3 is substantially that of a generally known compression valve, generally designated at 54. This valve includes a gripper 55, which is a compressible elongated-width washer. A gripper knob 56 engages the gripper 55 and applies a squeezing force thereto when the gripper knob is screwed on a threaded member 57 of the crimper. Such threading causes the internal surface 58 of the gripper 55 to move inwardly and thus grip an external portion of the catheter 24.

An alternative gripping arrangement is illustrated in FIG. 7 and FIG. 8. An entry end housing portion 61 incorporates a spring clamp member 62 which passes through a slot 63 of this housing portion. When the spring clamp member is in its raised orientation as shown, an internal gripper portion 64 will engage and hold a catheter (not shown) which has been slid over the guide member 44. When the spring clamp member is depressed, such as by pressing on knurled surface 65, the spring clamp member moves generally downwardly in order to remove its grip on the catheter, thereby providing for its easy entry and removal as desired. In the illustrated example, the spring action is achieved by a living hinge or joint 66 by which the spring clamp member 62 is mounted.

Figure 11:
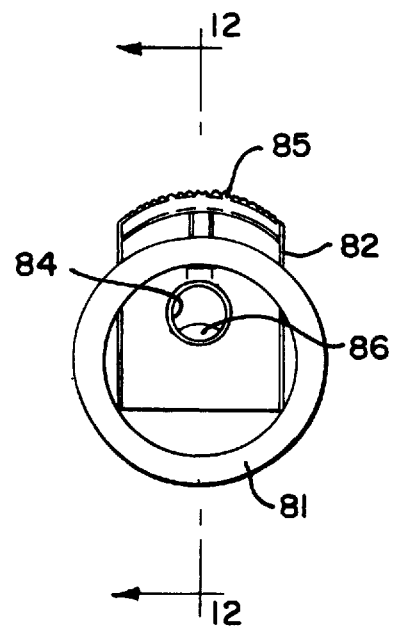
FIG. 11 is an end view of the embodiment of FIG. 10, shown in its gripping orientation.
Figure 12:
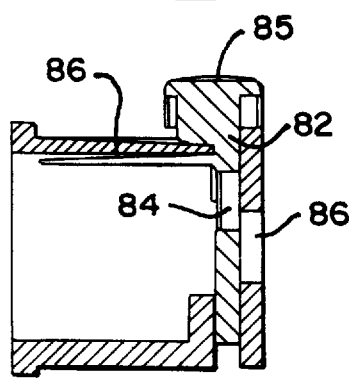
FIG. 12 is a cross-sectional view along the line 12—12 of FIG. 11.
Figure 13:
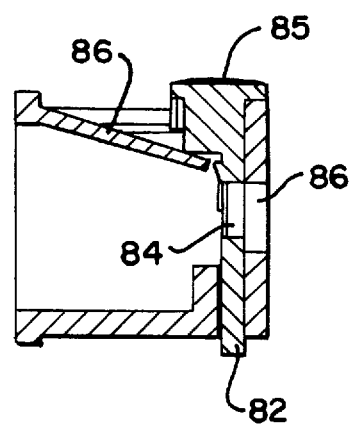
FIG. 13 is a view similar to FIG. 12 and illustrates the non-gripping orientation of this embodiment.

FIGS. 10, 11, 12 and 13 show another gripping arrangement. This entry end housing portion 81 incorporates a slidable clamp member 82 which passes through a slot 83 of this housing portion. When the slidable clamp member 82 is in its raised orientation as shown in FIGS. 10, 11 and 12, an internal gripping opening 84 will engage and hold a catheter (not shown) which has been slid over the guide member 44. When the slidable clamp member 82 is depressed as shown in FIG. 13, such as by pressing on knurled surface 85, the slidable clamp member is moved inwardly, the internal gripping opening 84 moves into general axial alignment with orifice 86 of the housing portion 81 in order to relieve the gripping action of the opening 84 on the catheter shaft. This latter orientation provides for easy entry and removal of the catheter from the crimping device. In this embodiment, the slidable clamp member 82 is biased in the gripping orientation by a finger 86 which is under tension as shown in FIG. 13 to return to its orientation shown in FIGS. 10, 11 and 12.

Whatever gripping assembly is used, the force provided by the gripping assembly should not be so tight as to prevent catheter rotation when crimping is proceeding. This ensures that the catheter will not be subjected to torsion forces that could twist it along its length and thus potentially deform or damage the catheter.

Discussing now the alignment approaches which can be used in order to ensure proper placement of the stent onto the balloon of the catheter, the diameter and length of the stent 48 contained within the crimper 21 may be marked on the device itself, the packaging or wrapping for the device, or on both. Additionally or alternatively, the outer case 22 could include external markings, for example arrowheads 71, to indicate the position of the stent with respect to the crimper 21. One manner of using these markings is as follows. The user positions the balloon of the catheter on the external surface of the outer case 22 such that the balloon is centered with respect to the arrowheads 71. Then, note is made of the location at which the shaft of the catheter lines up with entry edge 72 of the crimper. In this manner, the user determines how far the catheter must be inserted into the crimper in order for the balloon to be properly positioned within the stent, and the user then inserts the catheter for that distance. The catheter is then held in place by a suitable gripping arrangement as previously discussed.

A variation on this positioning approach is to provide a guide slot 73 (FIG. 2), which is an added element to facilitate determining the depth to which the catheter must be inserted into the device in order to properly position the balloon with respect to the stent. Markings 74 within this guide slot designate the location of the stent. In a manner somewhat similar to use of the arrowheads 71, the user will position the catheter such that its balloon is generally centered with respect to these markings 74, and appropriate steps will be taken to note the location on the catheter shaft which lines up with the entry edge 72 of the crimper.

When the catheters are of a known type, such as those having a marker band at a particular location on the catheter, this marker band can be positioned so that same is flush with the entry edge 72, for example, of the crimper. When these features are present, the balloon and stent will be properly aligned by simply inserting the catheter as far as possible into the crimper.

With respect to materials out of which various components can be made, preferably the materials will be relatively inexpensive and safely disposable. Materials of particular interest are those out of which the elongated wrapping member or belt 26 and the stent holding member or sheath 45 are made. It is generally preferred that the sleeve be somewhat softer than the belt. Sleeve and belt typically will be of approximately the same thickness, generally between about 0.002 inch and about 0.005 inch (from about 0.05 mm to about 0.13 mm). Materials used for the belt and the sheath should be biocompatible and sterilizable. An especially suitable belt material has been found to be polyethylene terephthalate. While the sheath may be made of any such suitable material, including various polymers and composites, shrink tubings having been found to be especially suitable. A useful material in this regard is polytetrafluoroethylene. This particular material provides stress and strain relief so that the stent will not be damaged. For example, after crimping, witness marks corresponding to the shape of the stent are visible on the sheath. Such sheath tubing will wrinkle or buckle or crumple when crimping is carried out, and it is soft enough so that it will not damage the stent within which it is in engagement during the crimping operation. Generally, the sheath tubing material will be more compliant than the belt material. The body or housing of the crimper is typically made of a polymer. When, for example, the stent or the like is radioactive, a more protective material, such as lead or a leaded material can be used.

Concerning the length of the holding member or sheath 45 and the width of the elongated wrapping member or belt 26, both should be longer than the length of the stent 48. For example, at a minimum, the belt should extend longer than the stent on both ends, such as by at least two or three millimeters at each end. This helps to assure uniform application of cylindrical forces along the entire length of the stent. Generally the belt width will be at least as great, preferably greater.

The crimping action in accordance with the present invention transforms a torsional load generated by digital twisting action by the user into a uniformly radially compressive force which is applied to substantially the entirety of the outer surface of the stent. This is illustrated in FIG. 5 and FIG. 6. When the user rotates the crimper knob 25, the belt 26 moves in the direction of the arrowhead of FIG. 5. Because of the drag along the trailing or downstream portion of the belt, tension, is developed along the belt. That tension is present along the looped path portion 37 of the belt. This exerts a force on the sheath 45 in a direction that is generally radial and toward the longitudinal feed axis 23. The illustrated stent 45 includes a plurality of open areas 50. It will be appreciated that, in this type of stent, these open areas will open even wider during deployment of the stent within the body vessel. In addition, they will generally close up during crimping. This closed-up condition of the stent 48 is illustrated in FIG. 6. It will also be noted that, in FIG. 6, the circumference of the sheath 45 has been reduced. Also reduced has been the outer circumference of the balloon 49 of the catheter.

As noted above, the crimper knob 25 and belt 26 move in the direction of the arrowhead of FIG. 5. Preferably, members are provided to prevent rotation in the opposite direction. Such an arrangement is shown in FIG. 9. Base member 28 includes a plurality of clutch teeth 76. Knob 25 incorporates clutch springs 77 which deflect as the knob is rotated and the clutch teeth alternatively engage and disengage when the knob is rotated in the designated direction. A "clicking" action and sound will be apparent. Ramps 78 are provided to permit knob rotation in only this one direction. Attempted rotation in the opposite direction will be prevented by engagement between the unramped ends 79 engaging an opposing face of one or more of the base member clutch teeth 76.

In the preferred operation of the crimper, the stent and the balloon generally rotate with the belt as it rides over them through the sheath. All spin in the same angular direction. This allows the balloon of the catheter to be folded over while the stent is being compressed and plasticly deformed onto the balloon. This provides a desirable folding of the balloon onto the catheter. Such is desirable because it achieves a more controlled opening of the balloon and the stent during deployment in vivo in the body vessel. In addition, the profile or outer diameter of the system comprising the stent and the balloon is reduced. The invention achieves a particularly uniform roll-up of the balloon and stent combination.

It will be appreciated that the belt thus applies the inwardly radially directed force on a large circumferential (and cylindrical) portion of the stent surface. It will further be appreciated that this belt arrangement can accommodate catheters, stents and sheaths which have a variety of sizes both before and after crimping. It is particularly to be noted that the belting arrangement has virtually no lower stent circumference limit inasmuch as the closure effect generated by this approach is limited only by the thickness of the assembly being crimped.

In connection with method and procedure aspects of the invention, the following is a preferred manner of assembling the stent into the sheath 45. First, the stent 48 is pre-crimped onto a mandrel. Then, the sheath is positioned over it, care being taken to ensure that the sheath extends beyond this stent on both ends. The sizing is such that the outside surface of the stent engages the inside surface of the sheath. Then the mandrel is removed. The result is along the lines of a stent within a straw. This assembly is then ready to be positioned within the case 22 of the crimper as previously discussed. Most notably, the leading end portion of this stent and sheath assembly can be inserted within an appropriate cylindrical opening of the base member 28. In this way, the stent and sheath assembly is supported externally, and the stent is positioned longitudinally in order to coincide with a predetermined position, such as between the arrowheads 71 or the markings 74. It is also desired that the sheath be secured at the cap member 29 so that it will remain within the case 22 of the crimper after crimping is completed and when the catheter is removed from the crimper. In this way, the stent which has been crimped onto the balloon of the catheter slides right out of the thus held sheath after crimping has been completed.

The crimper allows the physician to crimp the stent therewithin onto an appropriate angioplasty balloon catheter as selected by the physician. This is done through very simple operations and without jeopardizing the safety or effectiveness of the crimper. It will be understood that the crimping onto the balloon is by compressing the stent at a theoretically infinite number of contact points with a uniform radial force by rotating the stent and the catheter balloon with the belt looped around the sheath and stationary rollers.

In use, the appropriate guide means located on the outside of the crimper, such as within a designated slot therefor, is utilized to determine the depth of penetration of the catheter into the device which is required to center the balloon within and with respect to the stent. Next, without applying the grip pressure afforded by the gripping mechanism, such as by depressing the spring clamp member 62, or the slidable clamp member 82, the angioplasty balloon catheter is inserted to the required depth. This insertion is by passing the internal lumen of the catheter over the guide member 44, which typically will have a diameter of between about 0.010 and about 0.035 inch (about 0.25 mm to about 0.9 mm). Then, the gripping mechanism is activated, by either releasing the spring clamp member 62 or the slidable clamp member 82 or by threading the gripper knob 56. This locks the angioplasty balloon catheter in place within the stent that is within the crimper.

While grasping the outer case 22 of the crimper, the drive wheel or crimper knob 25 is rotated, and rotation is continued in the same direction until the crimper knob spins freely. This signals that crimping of the stent onto the balloon has been completed. The gripping mechanism is disengaged, and the angioplasty balloon catheter having the stent crimped onto its balloon is withdrawn from the crimper. At this stage, the crimper can be properly disposed of, and the balloon catheter and stent combination can be inspected for leaks, positioning and tightness of the catheter onto the balloon.

During the crimping operation, the user will experience the following during crimping by rotation of the knob. Initially, very little force will be required to rotate the knob while tension is developed along the belt. This can be considered to be a neutral position, and no force is being applied onto the stent or the underlying balloon catheter at this stage. Continued rotation of the knob gradually crimps the stent onto the catheter, and a noticeably increased effort will be encountered as the user continues to rotate the knob. Eventually, crimping will be completed, and the neutral position and feel during rotation of the knob will return. Thus, the crimping operation is extremely simple. The user need only continue to rotate in the same direction, and the end of crimping is signalled by having the knob spin freely.

It will be understood that the embodiments of the present invention which have been described are illustrative of some of the applications of the principles of the present invention. Numerous modifications may be made by those skilled in the art without departing from the true spirit and scope of the invention.

We claim:

1. A crimper for receiving a catheter and for placing and crimping a balloon-deployable device onto a catheter, the crimper comprising:

a guide member having a longitudinal axis generally coinciding with a longitudinal feed axis of the crimper;

a holding member positioned with respect to said guide member so as to accommodate a balloon-deployable device such as a stent and a catheter slidingly inserted along said guide member, into said crimper, and into a balloon-deployable device along said crimper longitudinal feed axis;

an elongated wrapping member which wraps substantially around said holding member so as to generally define a substantially cylindrical compression site lying along said longitudinal feed axis of the crimper; and a moving and guiding assembly along which the elongated wrapping member passes and by which the elongated wrapping member imparts a cylindrical compressive force onto said holding member and a balloon-deployable device positioned therewithin, whereby a balloon-deployable device is crimped onto the catheter.

2. The crimper in accordance with claim 1, wherein said moving and guiding assembly includes a pair of pinch rollers over which the elongated wrapping member is fed, and said substantially cylindrical compression site is along a portion of the elongated wrapping member which moves between the pair of pinch rollers.

3. The crimper in accordance with claim 2, wherein said substantially cylindrical compression site is at a loop of the elongated wrapping member.

4. The crimper in accordance with claim 3, wherein said elongated wrapping member is a belt and said holding member is a sheath.

5. The crimper in accordance with claim 1, wherein said moving and guiding assembly includes a drive shaft and knob assembly which is rotatable within the crimper by manual turning of said knob, and one end of said elongated wrapping member is secured to said drive shaft.

6. The crimper in accordance with claim 5, further including clutch components which permit rotation of the drive shaft and knob assembly in one direction and prevent rotation thereof in an opposite direction.

7. The crimper in accordance with claim 1, wherein said moving and guiding assembly further includes a member for imparting frictional drag onto a trailing portion of the elongated wrapping member.

8. The crimper in accordance with claim 1, wherein said moving and guiding assembly includes a drive shaft and knob assembly which is rotatable within the crimper by manual turning of said knob, one end of said elongated wrapping member is secured to said drive shaft, and said moving and guiding assembly further includes a member for imparting frictional drag onto a trailing portion of the elongated wrapping member.

9. The crimper in accordance with claim 2, wherein said moving and guiding assembly includes a drive shaft and knob assembly which is rotatable within the crimper by manual turning of said knob, one end of said elongated wrapping member is secured to said drive shaft, and said moving and guiding assembly further includes a member for imparting frictional drag onto a trailing portion of the elongated wrapping member.

10. The crimper in accordance with claim 4, wherein said moving and guiding assembly includes a drive shaft and knob assembly which is rotatable within the crimper by manual turning of said knob, one end of said elongated wrapping member is secured to said drive shaft, and said moving and guiding assembly further includes a member for imparting frictional drag onto a trailing portion of the elongated wrapping member.

11. The crimper in accordance with claim 1, wherein said guide member is a guide wire located along said longitudinal feed axis, said holding member is a sheath, a cylindrical space is provided between the guidewire and the sheath, and the catheter is slidably accommodated within said cylindrical space.

12. The crimper in accordance with claim 11, further including a stent as a balloon-deployable device, said stent having an outside surface which engages an inside surface of the sheath, and wherein said cylindrical space is defined between an inside surface of the stent and said guide wire.

13. The crimper in accordance with claim 1, further including markings on an external portion of the crimper, which markings indicate the position of a balloon-deployable device within said crimper.

14. The crimper in accordance with claim 1, further including a gripping mechanism at an entry end portion of said crimper, said gripping mechanism applying a generally radially directed gripping force onto a catheter positioned within the crimper.

15. The crimper in accordance with claim 14, wherein said gripping mechanism applied gripping force permits catheter rotation in response to movement of said elongated wrapping member along said holding member.

16. The crimper in accordance with claim 15, wherein said gripping mechanism includes a movable clamp member which is biased for applying the generally radially directed gripping force.

17. The crimper in accordance with claim 1, wherein said holding member is made of a material which is more compliant than material of said elongated wrapping member.

18. A crimper for receiving a catheter and for placing and crimping a balloon-deployable device onto a catheter, the crimper comprising:
   a guide member having a longitudinal axis generally coinciding with a longitudinal feed axis of the crimper;
   a holding sheath positioned with respect to said guide member so as to accommodate balloon-deployable device such as a stent and a catheter slidingly inserted along said guide member, into said crimper, and into said balloon-deployable device along said crimper longitudinal feed axis;
   an elongated wrapping belt which wraps around substantially the circumference of said holding sheath so as to generally define a substantially cylindrical compression belt loop lying along said longitudinal feed axis of the crimper; and
   a moving and guiding assembly by which the elongated wrapping belt imparts a cylindrical compressive force onto said holding sheath and said balloon-deployable device positioned therewithin, whereby the balloon-deployable device is crimped onto the catheter, said moving and guiding assembly including a pair of pinch rollers over which the elongated wrapping belt is fed, said substantially cylindrical compression belt loop being between the pair of pinch rollers, said moving and guiding assembly further including a drive shaft and knob assembly which is rotatable within the crimper by manual turning of said knob, a leading end of said elongated wrapping belt being secured to said drive shaft, and a trailing length of the elongated wrapping belt engages a member for imparting frictional drag onto the trailing length of the elongated wrapping belt.

19. The crimper in accordance with claim 18, wherein said member for imparting frictional drag onto the elongated wrapper member is a rod over which said elongated wrapping belt passes.

20. The crimper in accordance with claim 19, further including a plurality of said rods, and said elongated wrapping belt is threaded between said rods.

21. The crimper in accordance with claim 18, further including a gripping mechanism at an entry end portion of said crimper, said gripping mechanism applying a generally radially directed force onto a catheter positioned within the crimper.

22. A crimper and balloon-deployable device, the crimper comprising:
   a balloon-deployable device such as a stent;
   a guide member having a longitudinal axis generally coinciding with a longitudinal feed axis of the crimper;
   a holding member positioned with respect to said guide member so as to accommodate said balloon-deployable device and a catheter slidingly inserted along said guide member, into said crimper, along said crimper longitudinal feed axis;
   an elongated wrapping member which wraps substantially around said holding member so as to generally define a substantially cylindrical compression site lying along said longitudinal feed axis of the crimper; and
   a moving and guiding assembly along which the elongated wrapping member passes and by which the elongated wrapping member imparts a cylindrical compressive force onto said holding member and said balloon-deployable device positioned therewithin, whereby said balloon-deployable device is crimped onto the catheter.

23. The crimper and device in accordance with claim 22, wherein said moving and guiding assembly includes a pair of pinch rollers over which the elongated wrapping member is fed, and said substantially cylindrical compression site is along a portion of the elongated wrapping member which moves between the pair of pinch rollers.

24. The crimper and device in accordance with claim 23, wherein said substantially cylindrical compression site is at a loop of the elongated wrapping member.

25. The crimper and device in accordance with claim 24, wherein said elongated wrapping member is a belt and said holding member is a sheath.

26. The crimper and device in accordance with claim 22, wherein said moving and guiding assembly further includes a member for imparting frictional drag onto a trailing portion of the elongated wrapping member.

27. The crimper and device in accordance with claim 22, wherein said balloon-deployable device has an inside surface and has an outside surface which engages an inside surface of said holding member, said guide member is a guide wire located along said longitudinal feed axis, a cylindrical space is provided between the guidewire and the sheath, said cylindrical space being defined by said inside surface of the balloon-deployable device and said guidewire, and the catheter is slidably accommodated within said cylindrical space.

28. A procedure for crimping a balloon-deployable device onto a catheter, comprising the steps of:

inserting a balloon-deployable device within a stent holding member so that the outside surface of the balloon-deployable device and the inside surface of holding member engage each other so as to provide an assembly of said balloon-deployable device and said holding member;

positioning said assembly within a crimper having an elongated wrapping member which engages the outside surface of the holding member;

inserting a catheter into the crimper and into the balloon-deployable device of said assembly;

moving the elongated wrapping member over the holding member while the elongated wrapping member imparts radially directed forces onto the holding member;

continuing said moving step until said radially directed forces collapse the holding member and the balloon-deployable device therewithin onto the catheter, thereby crimping the balloon-deployable device onto the catheter; and withdrawing from the crimper the catheter and the balloon-deployable device crimped thereonto.

29. The procedure in accordance with claim 28, wherein the inserting step aligns a balloon of the catheter with the balloon-deployable device such that the balloon-deployable device overlies at least a portion of the balloon.

30. The procedure in accordance with claim 28, wherein, during said removing step, the holding member remains within the crimper and is thereby separated from the balloon-deployable device which has been crimped onto the catheter.

31. The procedure in accordance with claim 28, wherein said moving step includes spinning a knob in order to rotate the elongated wrapping member around a drive shaft.

32. The procedure in accordance with claim 28, further including mechanically gripping a portion of the catheter prior to said moving step.

33. The procedure in accordance with claim 29, further including designating the location of the balloon-deployable device within the crimper, and utilizing said designating step in order to position the balloon of the catheter with respect to the balloon-deployable device such that the longitudinal center of the balloon-deployable device and the longitudinal center of the balloon generally coincide.

* * * * *

UNITED STATES PATENT AND TRADEMARK OFFICE
CERTIFICATE OF CORRECTION

PATENT NO. : 5,836,952
DATED : November 17, 1998
INVENTOR(S) : Horace R. Davis and Phillip G. Reed It is certified that error appears in the above-identified patent and that said Letters Patent is hereby corrected as shown below:

Col. 4, line 36, "detail" should read --detailed--;
    line 38, "detail" should read --detailed--.
Col. 8, line 13, "tension, is" should read --tension is--.
Col. 11, line 52, "accommodate balloon-deployable" should read --accommodate a balloon-deployable--.

Signed and Sealed this

Eighteenth Day of July, 2000

Attest:

Q. TODD DICKINSON

*Attesting Officer*     *Director of Patents and Trademarks*